US009427348B2

(12) United States Patent
Matthews et al.

(10) Patent No.: US 9,427,348 B2
(45) Date of Patent: Aug. 30, 2016

(54) ORTHOTIC SYSTEM AND METHOD UTILIZING HYDROSTATIC COMPRESSION OF SOFT TISSUE TO UNLOAD THE KNEE AND/OR HEEL UP TO 100%

(71) Applicants: Kevin C. Matthews, San Antonio, TX (US); Alexander N. Leos, San Antonio, TX (US)

(72) Inventors: Kevin C. Matthews, San Antonio, TX (US); Alexander N. Leos, San Antonio, TX (US)

( * ) Notice: Subject to any disclaimer, the term of this patent is extended or adjusted under 35 U.S.C. 154(b) by 135 days.

(21) Appl. No.: 13/960,329

(22) Filed: Aug. 6, 2013

(65) Prior Publication Data

US 2014/0276303 A1 Sep. 18, 2014

Related U.S. Application Data

(60) Provisional application No. 61/785,668, filed on Mar. 14, 2013.

(51) Int. Cl.
*A61F 5/00* (2006.01)
*A61F 5/01* (2006.01)
*A61F 5/34* (2006.01)

(52) U.S. Cl.
CPC ............ *A61F 5/0111* (2013.01); *A61F 5/0102* (2013.01); *A61F 5/012* (2013.01); *A61F 5/34* (2013.01)

(58) Field of Classification Search
CPC .............. A61F 5/0102; A61F 5/0125; A61F 2005/0151; A61F 2005/0162; A61F 5/0127; A61F 2005/0158; A61F 2005/0167; A61F 5/0111; A61F 5/012; A61F 5/0123; A61F 5/34; A61F 2005/0165; A61F 2005/0137; A61F 2005/0139; A61H 1/0255; A63B 21/00178; A41D 13/0007; A41D 1/06; A41D 1/14; A41D 1/22; A41D 2400/38; A41D 27/02; A62B 35/0025; A62B 17/003; A62B 35/0006
USPC .......................... 602/16, 23, 26–27; 128/882
See application file for complete search history.

(56) References Cited

U.S. PATENT DOCUMENTS

| 4,632,096 | A | * | 12/1986 | Harris | ............................. 602/16 |
| 4,693,239 | A | | 9/1987 | Clover, Jr. | |
| 5,092,321 | A | | 3/1992 | Spademan | |
| 5,344,390 | A | * | 9/1994 | Motloch | ........................... 602/23 |
| 5,370,133 | A | | 12/1994 | Darby et al. | |
| 5,453,075 | A | | 9/1995 | Bonutti et al. | |
| 5,501,659 | A | * | 3/1996 | Morris | .................. A61F 5/0111 128/882 |
| 5,571,206 | A | * | 11/1996 | Varn | ............................... 623/27 |
| 6,010,474 | A | | 1/2000 | Wycoki | |
| 6,021,780 | A | | 2/2000 | Darby | |
| 6,334,854 | B1 | | 1/2002 | Davis | |

(Continued)

*Primary Examiner* — Michael Brown
(74) *Attorney, Agent, or Firm* — Kammer Browning PLLC

(57) ABSTRACT

An orthotic system and method for a knee ankle foot orthosis (KAFO) or ankle foot orthosis (AFO) capable of removing up to 100% of the weight-bearing forces at the knee and tibia and/or ankle and heel. The KAFO and AFO of the present invention utilize a fully adjustable compound closure system and compression liner to circumferentially compress the soft tissue of the thigh or calf to reduce loading forces on the leg at all points distal to the distal border of the compression liner. The degree of reduction in weight-bearing is adjusted by applying the orthosis with the heel of the individual raised above the foot platform, tightening the compound closure system, allowing the tissue to drop down within the compression liner, assessing the position of the heel above the foot platform, and adjusting the compound closure system to maintain the desired degree of elevation of the heel above the foot platform.

10 Claims, 8 Drawing Sheets

(56) References Cited

U.S. PATENT DOCUMENTS

| | | | |
|---|---|---|---|
| 8,827,941 B2 * | 9/2014 | Davis et al. | 602/62 |
| 2002/0128574 A1 | 9/2002 | Darby | |
| 2007/0276307 A1 | 11/2007 | Erenstone | |
| 2010/0106065 A1 | 4/2010 | Ward | |
| 2013/0267878 A1 * | 10/2013 | Franke | A61F 5/0111 602/7 |

* cited by examiner

ORTHOTIC SYSTEM AND METHOD UTILIZING HYDROSTATIC COMPRESSION OF SOFT TISSUE TO UNLOAD THE KNEE AND/OR HEEL UP TO 100%

CROSS REFERENCE TO RELATED APPLICATIONS

This application claims the benefit under Title 35 United States Code §119(e) of U.S. Provisional Patent Application Ser. No. 61/785,668 filed Mar. 14, 2013, the full disclosure of which is incorporated herein by reference.

BACKGROUND OF THE INVENTION

1. Field of the Invention

The present invention relates generally to orthotic designs for lower limb orthopedic devices. The present invention relates more specifically to an orthotic system and method utilizing hydrostatic compression of soft tissue to remove the load bearing forces of the knee and/or distal tibia, talus, and heel up to 100%.

2. Description of the Related Art

There are a number of medical conditions in which load bearing on an affected structure is contraindicated. Injuries such as fractures of the talus, comminuted fractures of the distal tibia or calcaneus, osteomyelitis infections, avascular necrosis of the talus, ulcerations, post surgical infections and some other acute conditions can be adversely impacted under the stress of weight bearing.

In the past, severe conditions of the knee, distal tibia, talus, or calcaneus may have been treated with immobilization and partial unloading by use of plaster-of-paris casts. These plaster casts, however, would be heavy and uncomfortable for the patient. More recently, either custom fabricated or prefabricated orthoses have been prescribed by physicians as a more lightweight and comfortable alternative to plaster casts. These orthoses also have the advantage of the capability to be removed by the patient at any time.

However, prior art custom fabricated and prefabricated orthoses both have their drawbacks. Prior art prefabricated orthoses are not capable of withstanding long periods of use, are very bulky which eliminates the possibility of normal footwear, and are not capable of 100% unloading of the desired structures. Prior art custom orthoses are capable of longer lengths of use and may be used with normal footwear, but these orthoses are very difficult to fabricate properly. Moreover, these designs tend to rely on achieving a purchase on proximal bones, rather than soft tissue, making them difficult to tolerate for extended periods.

A commonly prescribed prefabricated orthosis is the Zero G. While the Zero G is capable of 100% unloading of the distal tibia, ankle and heel, it is not applicable toward conditions of the knee. Also, this brace is very bulky and will not allow the use of normal footwear on the braced side. The Zero G is designed for temporary use of just a few months and will not hold up to the rigors of every day activity.

One of the most frequently prescribed custom orthoses to offload the distal tibia, ankle, and heel is the patellar tendon bearing (PTB) orthosis. The PTB orthosis is a well known design which transfers weight through the patellar tendon and onto the orthopedic device similar to the approach used in below knee prosthetic devices. PTBs are difficult to fabricate and often not tolerated due to the pressures and forces needed to achieve the desired outcome, removing all load bearing forces of the distal tibia and below. In prosthetics, the PTB type prosthesis is better tolerated as these forces are only present in weight bearing. As soon as weight is removed from the extremity the pressures dissipate. In orthotics this is not the case.

While the Zero G, PTB orthosis, and other such prior art devices can sometimes be successful in treating these types of conditions, they all have major drawbacks. Also, the majority of options currently available are only applicable to the lower leg and none are capable of 100% unloading of the knee during ambulation.

In many situations complete unloading may be recommended but the patient may not have a lifestyle that allows for such limited ambulation, and because there is currently no orthopedic device available that allows for ambulation while unloading the knee, distal tibia, talus, or heel up to 100% without major drawbacks, there is need for a device specifically designed to unload the desired structures up to 100% with more benefits and fewer drawbacks than prior art designs.

SUMMARY OF THE INVENTION

In fulfillment of the above objectives, the present invention provides an orthotic system and method utilizing hydrostatic compression of soft tissue to unload the knee and/or heel up to 100% as it may be applied to a Knee Ankle Foot Orthosis (KAFO) or an Ankle Foot Orthosis (AFO). In general, the design is comprised of a shell containing a compression liner which circumferentially captures and compresses the conical shape of either the distal thigh or distal calf, thereby supporting any weight proximal to the point of compression and unloading the entire limb distal to the point of compression up to 100%.

Specifically, this design can be used to unweight the knee and ankle by capturing the conical shape of the distal end of the thigh or to unweight the ankle only by capturing the conical shape of the distal end of the calf 100% unloading may be easily achieved in any situation using this design, but the amount of circumferential compression applied is fully adjustable which allows the amount of unloading to be fully adjustable, from 0% up to 100% and including any amount in between. The orthotic design of the present invention is easier to fabricate and duplicate than those in the prior art. The design is well tolerated due to adjustability of compression force and the ability to make adjustments for comfort, control, and loading requirements to meet the needs of the individual patient.

Further objectives of the present invention will become apparent from an understanding of the following detailed description and the attached drawing figures which may be briefly described as follows.

DETAILED DESCRIPTION OF THE PREFERRED EMBODIMENTS

The present invention discloses an orthotic design utilizing hydrostatic compression of soft tissue to unload the knee and/or heel up to 100% as it may be applied to a Knee Ankle Foot Orthosis (KAFO) or an Ankle Foot Orthosis (AFO). In general, the design is comprised of a shell containing a compression liner which circumferentially captures and compresses the conical shape of either the distal thigh or distal calf, thereby supporting any weight proximal to the point of compression and unloading the entire limb distal to the point of compression up to 100%. The fully adjustable amount of circumferential compression applied allows the amount of weight bearing to be fully adjustable, from 0% up to 100%. The design is also adjustable for comfort, control, and loading requirements to meet the needs of the individual patient.

Knee Ankle Foot Orthotic System

Figure 1A:
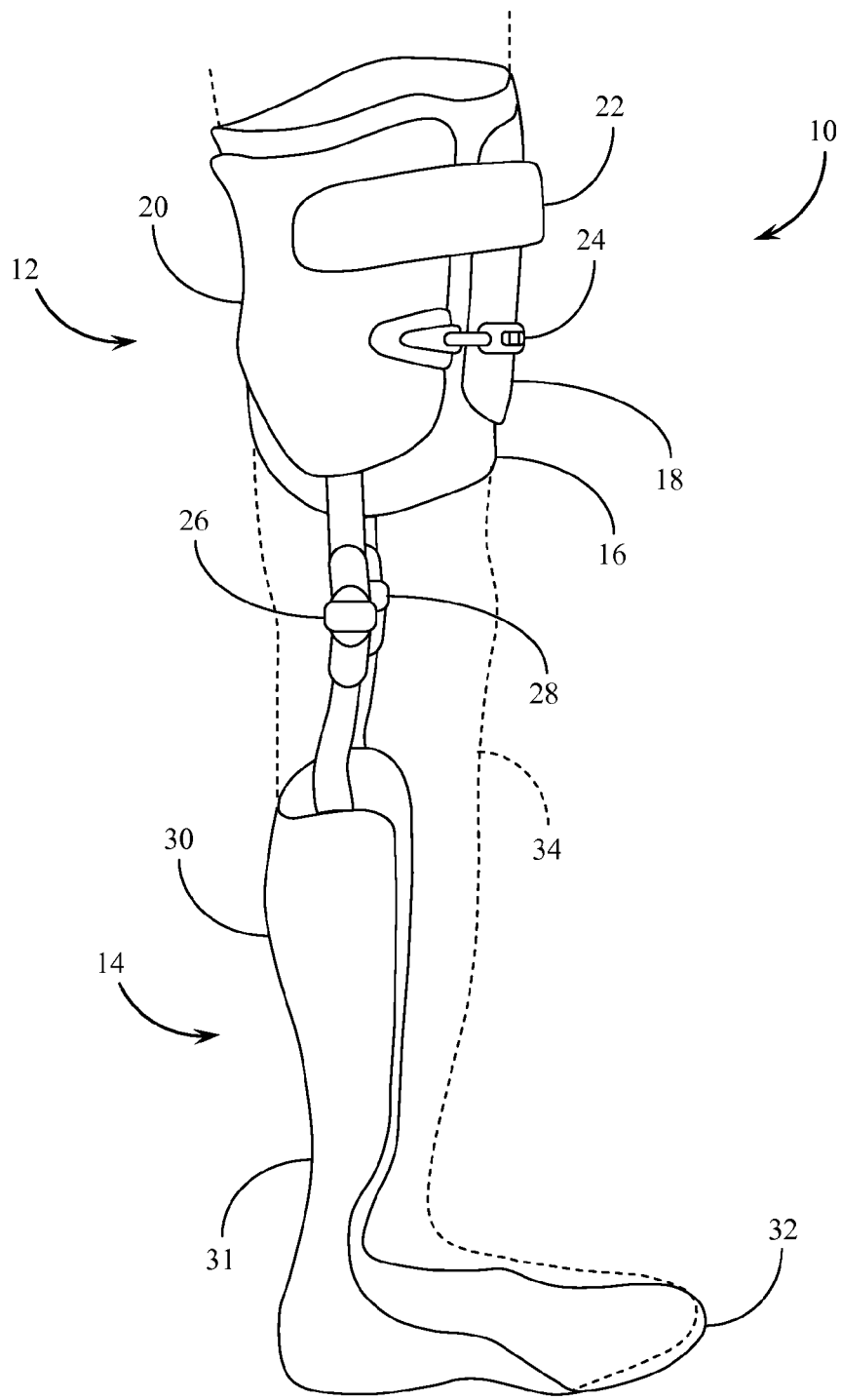
FIG. 1A is a diagram of the knee/ankle/foot orthotic system of the present invention.

Reference is made first to FIG. 1A for a description of the orthotic design for the knee/ankle/foot orthotic system of the present invention. The ideal design as applied to a KAFO 10 is shown in FIG. 1A. The design is similar to traditional KAFOs in appearance and component parts. FIG. 1A provides an overview of the KAFO 10 and the configuration of its component parts. As shown, the KAFO is comprised of a thigh shell assembly 12 which has an anterior portion 18 and a posterior portion 20. The thigh shell compression liner 16 is in direct contact with the leg 34. These components are held in place with the proximal 22 and distal 24 compound closure system. The thigh shell assembly 12 for the KAFO is connected to the calf shell assembly 14 by metal uprights with medial 26 and lateral 28 locking knee joints. The calf shell assembly 14 is composed of a calf portion 30, an ankle portion 31, and a foot platform 32.

Figure 3A:
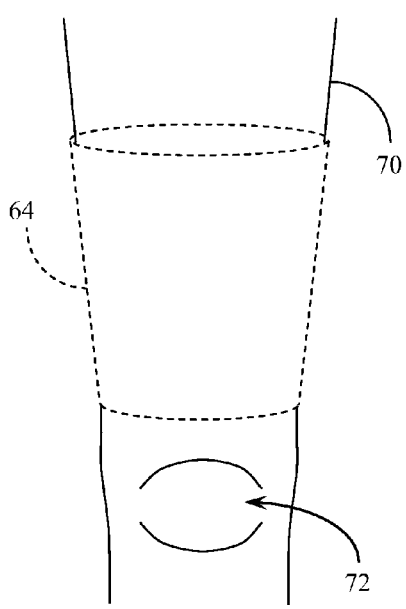
FIG. 3A is a diagram of the thigh compression area of the knee/ankle/foot orthotic system of the present invention.

The design of the present invention can be used to unweight the knee and ankle by capturing the conical shape of the distal end of the thigh as shown in FIG. 3A. FIG. 3A is a diagram of the thigh compression area of the knee/ankle/foot orthotic system of the present invention. FIG. 3A shows the area of compression 64 on the distal end of the thigh 70 above the knee 72. 100% unloading may be easily achieved in any situation using this design, but the amount of circumferential compression applied is fully adjustable which allows the amount of unloading to be fully adjustable, from 0% up to 100% and including any amount in between.

Figure 3B:
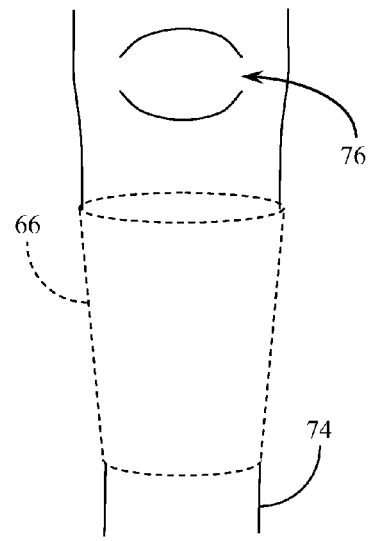
FIG. 3B is a diagram of the calf compression area of the ankle/foot orthotic system of the present invention.
Figure 3C:
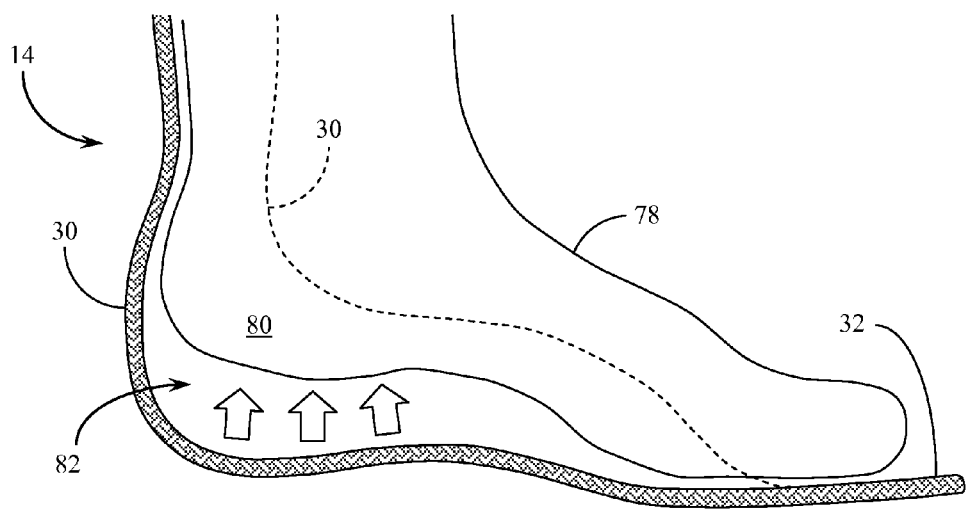
FIG. 3C is a diagram of the elevation of the heel over the foot platform of the orthotic system of the present invention.

FIG. 3C is a diagram of the elevation of the heel over the foot platform of the orthotic system of the present invention. FIG. 3C shows the entire limb distal to the point of compression fully unloaded 82. Specifically, FIG. 3C shows a portion of the calf shell assembly for KAFO 14, the calf portion of the ankle foot shell 30, and the foot platform of the ankle foot shell 32. The foot 78 and heel 80 are shown in the foot platform 32. FIG. 3C demonstrates the 100% unloading of the calf by the elevation 82 of the heel 80 over the foot platform 32.

Figure 4A:
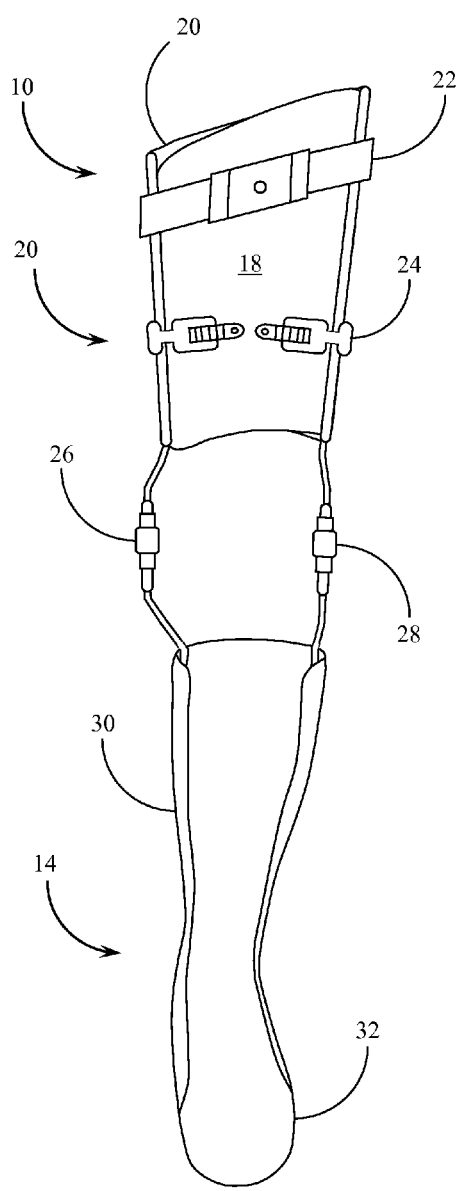
FIG. 4A is a diagram of the frontal view of the knee/ankle/foot orthotic system of the present invention.

FIG. 4A is a diagram of the frontal view of the knee/ankle/foot orthotic system of the present invention. As shown in FIG. 4A, the KAFO 10 utilizes a thigh shell comprised of posterior 20 and anterior 18 sections, an ankle-foot shell 14, two metal uprights with medial 26 and lateral 28 locking knee joints, and proximal 22 and distal 24 compound closure systems for containing and compressing the soft tissue at the thigh.

Figure 4B:
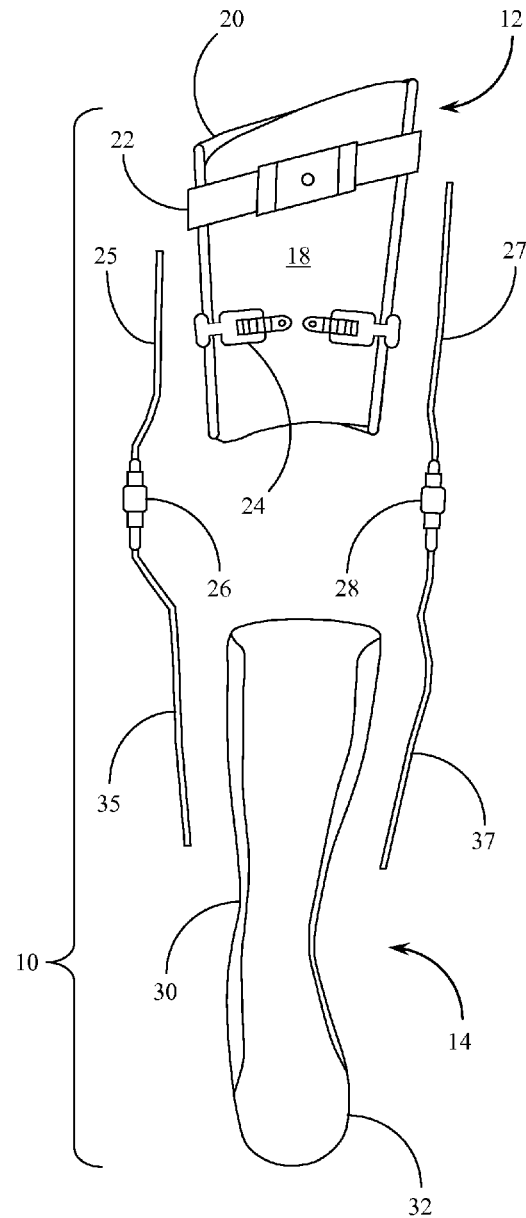
FIG. 4B is a diagram of the frontal view of the separate components of the knee/ankle/foot orthotic system of the present invention.

FIG. 4B is a diagram of the frontal view of the separate major components of the knee/ankle/foot orthotic system of the present invention: the thigh shell assembly 12, the calf shell assembly 14, and the metal uprights. The metal uprights are composed of medial 25 and lateral 27 thigh uprights, medial 35 and lateral 37 calf uprights, and medial 26 and lateral 28 locking knee joints.

Figures 4C, 4D:
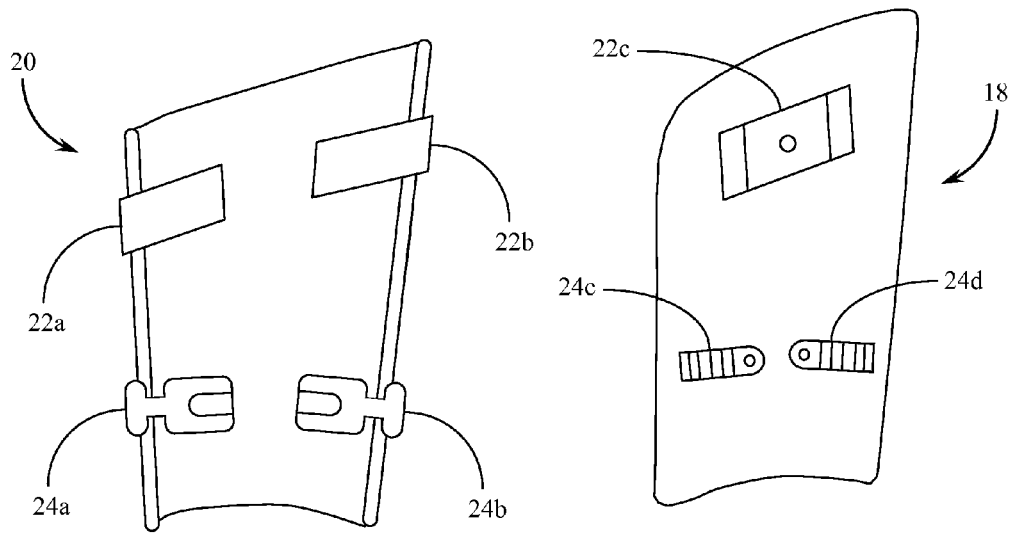
FIG. 4C is a diagram of the posterior portion of the thigh shell of the knee/ankle/foot orthotic system of the present invention.
FIG. 4D is a diagram of the anterior portion of the thigh shell of the knee/ankle/foot orthotic system of the present invention.

The thigh shell is ideally fabricated from carbon fiber to achieve high strength with minimal weight, but may also be fabricated from plastic or other similar materials. The thigh shell is comprised of two sections, a posterior shell and an anterior shell. FIG. 4C is a diagram of the posterior portion 20 of the thigh shell of the knee/ankle/foot orthotic system of the present invention. The posterior shell should be rigid and will be mounted securely to the metal uprights by means of rivets or similar fasteners. The posterior shell will contain the thigh and transfer weight away from the distal limb and through the metal uprights into the ankle-foot section and to the ground. The posterior thigh shell should cover the majority of the thigh circumferentially and enough of the height of the thigh to properly encompass the conical shape of the thigh.

Figure 4E:
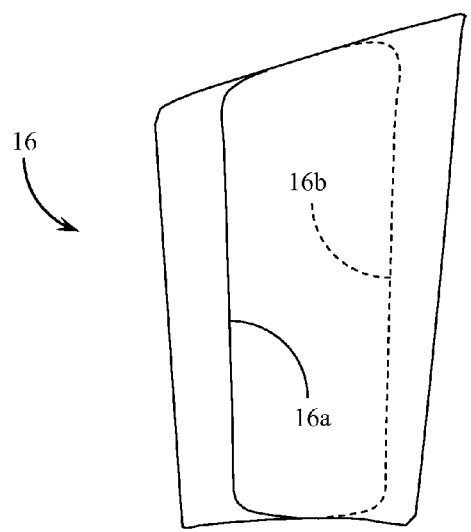
FIG. 4E is a diagram of the thigh shell compression liner of the knee/ankle/foot orthotic system of the present invention.

FIG. 4D is a diagram of the anterior portion 18 of the thigh shell of the knee/ankle/foot orthotic system of the present invention. The rigidity of the anterior shell is less important and may vary, as this shell's purpose is only to contain the soft tissue and act as an interface between the compound closure system and the compression liner. FIG. 4E is a diagram of the thigh shell compression liner 16 of the knee/ankle/foot orthotic system of the present invention showing both the interior ends 16a and exterior ends 16b of the liner which encompasses the thigh and overlaps anteriorly.

The anterior thigh shell should cover the minority of the thigh circumferentially and enough of the height of the thigh to properly encompass the conical shape of the thigh. The thigh shell should be made to a model of the patient's leg for optimal outcome, using industry standard laminating/fabricating procedures.

The ankle-foot shell of the knee/ankle/foot orthotic system is ideally fabricated from carbon fiber to achieve high strength with minimal weight, but may also be fabricated from plastic or other similar materials. The ankle-foot shell should be rigid and will be mounted securely to the metal uprights by means of rivets or similar fasteners. The design of the ankle-foot section is unimportant and may vary as long as it can effectively contain the lower limb and transfer weight from the metal uprights to the ground. The standard design is one solid shell encompassing the posterior of the lower limb, the plantar surface of the foot, and enough of the medial and lateral surfaces of the lower limb and foot to contain the lower limb and foot.

Alternatively, the ankle-foot shell could be comprised of (1) two sections, a calf section and a foot section with the metal uprights fastened to the calf section and the metal uprights terminating into ankle joints which interface with stirrups fastened to the foot section or (2) any other variation that could effectively contain the lower limb and transfer weight from the metal uprights to the ground. The ankle-foot shell should be made to a model of the patient's leg for optimal outcome, using industry standard laminating/fabricating procedures.

Figure 2A:
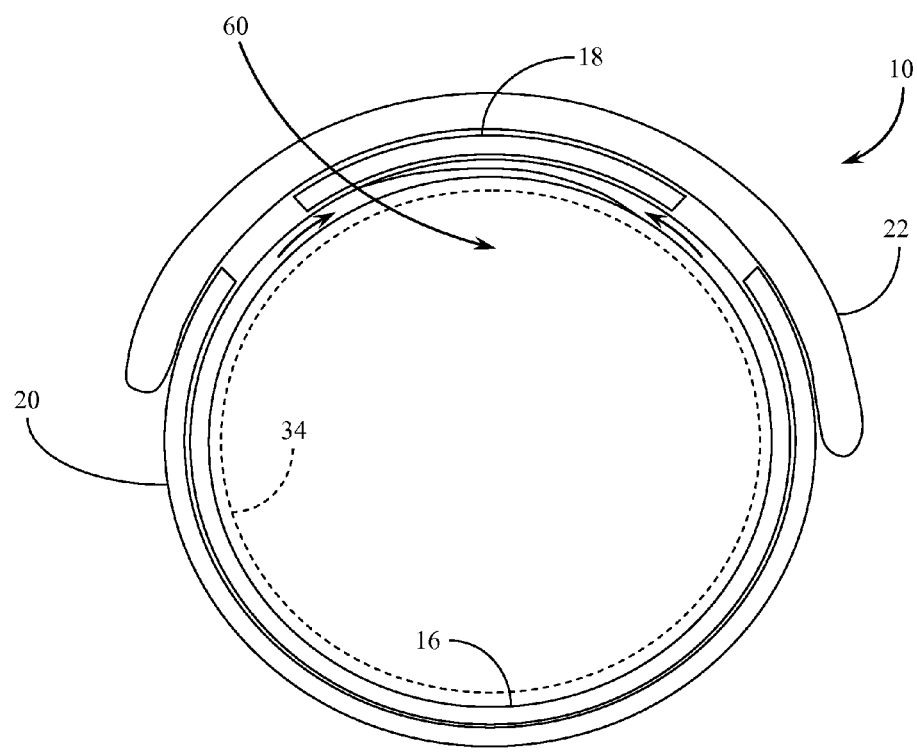
FIG. 2A is a diagram of the top view of the complete thigh shell of the knee/ankle/foot orthotic system of the present invention.

The compression liner is ideally fabricated from a 35 durometer Ethylene-Vinyl Acetate for flexibility, comfort, and ease of fabrication, but may also be fabricated from other foam, plastic, or similar materials. FIG. 2A is a diagram of the top view of the complete thigh shell of the knee/ankle/foot orthotic system 10 of the present invention. FIG. 2A shows the leg 34 and the point of entry on the thigh shell 60. The thigh shell compression liner 16 is fitted to the posterior thigh shell 20. The compression liner should be fastened to the posterior thigh shell by means of rivets or similar fasteners. The compression liner 16 should extend slightly beyond the distal and proximal edges of the posterior thigh section and circumferentially should overlap anteriorly beneath the anterior portion of the thigh shell 18.

The entire configuration is secured by the proximal compound closure system 22. When the compound closure system is tightened, the compression liner overlap will increase, allowing for varying degrees of circumferential compression control. The compression liner should be made to a model of the patient's leg for optimal outcome, using industry standard fabricating procedures.

There are two metal uprights with knee joints that lock using the commonly known drop-lock system. The joint heads are steel, while the uprights themselves should ideally be aluminum. Aluminum is lighter weight than other available upright metals but is strong enough to support most patients. Otherwise, steel or titanium uprights may be used. The uprights attach medially and laterally to the posterior thigh shell and the ankle-foot shell by means of rivets or similar fasteners as in any standard KAFO design. The upright knee joints should be centered over the patient's mechanical knee joint. The purpose of the metal uprights is to transfer weight from the posterior thigh shell to the ankle-foot shell and to allow for controlled knee motion (i.e., can be unlocked for sitting). The metal uprights should be contoured to a model of the patient's leg for optimal outcome, using industry standard fabricating procedures.

As shown in FIG. 4C, the compound closure system is composed of proximal and distal closure elements. These closures may be of varying types known in the art. However, in a preferred embodiment, the compound closure system consists ideally of two distal ratcheting ski-buckle type straps (also known as ladder straps) and two proximal hook and loop type straps which attach anteriorly to the anterior thigh shell and medially and laterally to the posterior thigh shell by means of rivets or similar fasteners. FIG. 4C shows the medial portion 22a and lateral portion 22b of these straps. The distal straps are ideally of the ratcheting type since compression of the distal thigh is more crucial to the efficacy of the design than compression of the proximal thigh. FIG. 4C shows the medial buckle 24a and lateral buckle 24b of these straps. The ratcheting or ladder straps take less effort to tighten and will maintain that tightened position better than hook and loop straps. However, the ratcheting straps may be difficult for the patient to align during donning and so simpler hook and loop straps are ideal proximally. FIG. 4D shows the anterior connector of the proximal compound closure system 22c and the straps 24c and 24d for the distal compound closure system.

However, any combination of ratcheting and/or hook and loop straps distally, proximally, medially, or laterally could conceivably be just as effective. The compound closure system, when tightened, will apply pressure through the anterior thigh shell and onto the compression liner which will then compress the soft tissue of the thigh. All elements are necessary for optimal function of the orthosis. Different materials may be used to accomplish the stated goal.

Ankle Foot Orthotic System

Figure 1B:
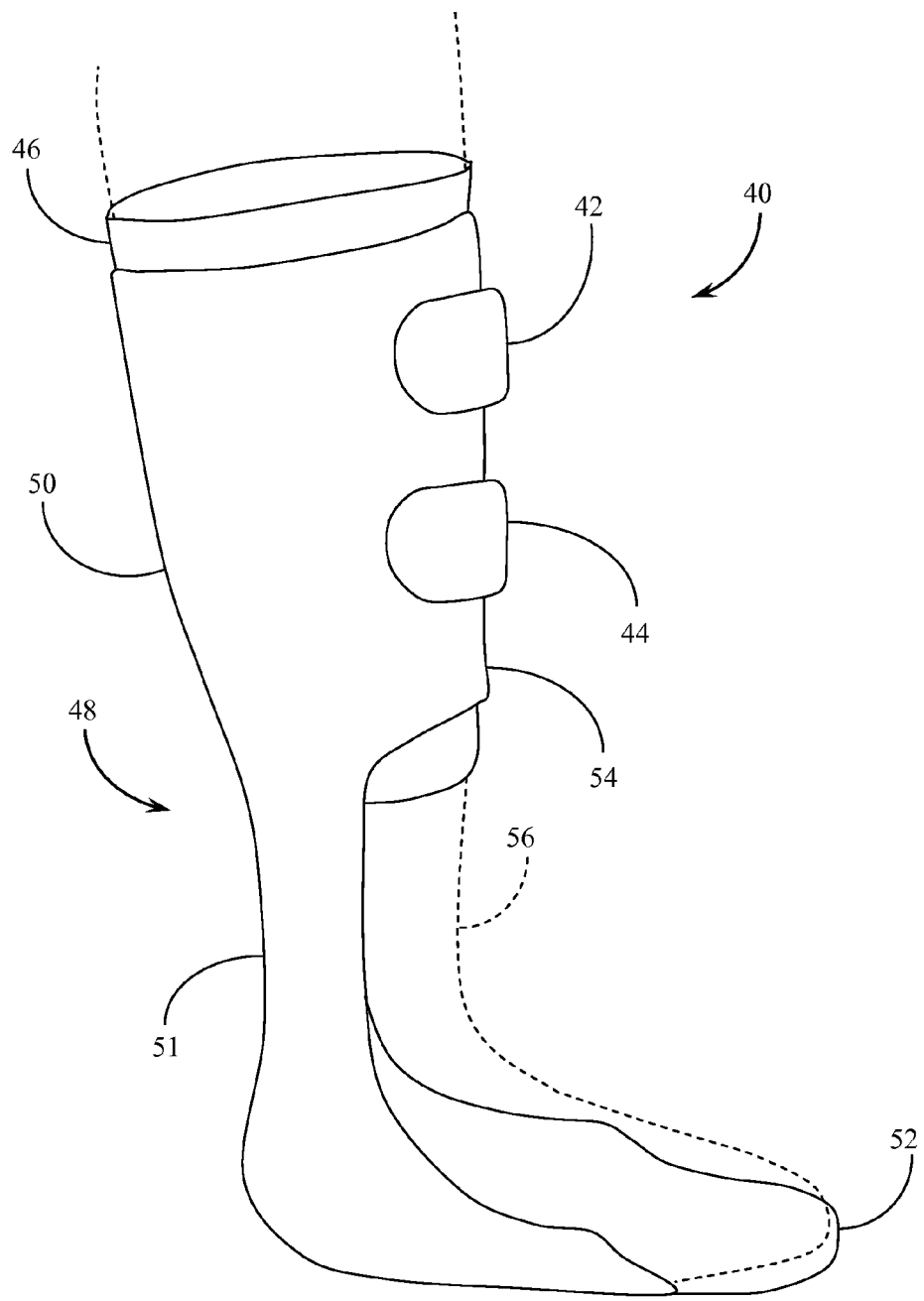
FIG. 1B is a diagram of the ankle/foot orthotic system of the present invention.

Reference is made first to FIG. 1B for a description of the orthotic design for the ankle/foot orthotic system of the present invention. The ideal design as applied to an AFO 40 is shown in FIG. 1B. The design is similar to traditional AFOs in appearance and component parts. FIG. 1B provides an overview of the AFO 40 and the configuration of its component parts. As shown, the AFO is comprised of an ankle foot shell assembly 48 which has an anterior portion 54 and a posterior portion 50, and an ankle portion 51 and a foot platform 52. As shown in FIG. 1B, it utilizes a compression liner 46 that encompasses the calf and overlaps, and proximal 42 and distal 44 compound closure systems for containing and compressing the soft tissue of the leg 56 at the calf.

Figure 2B:
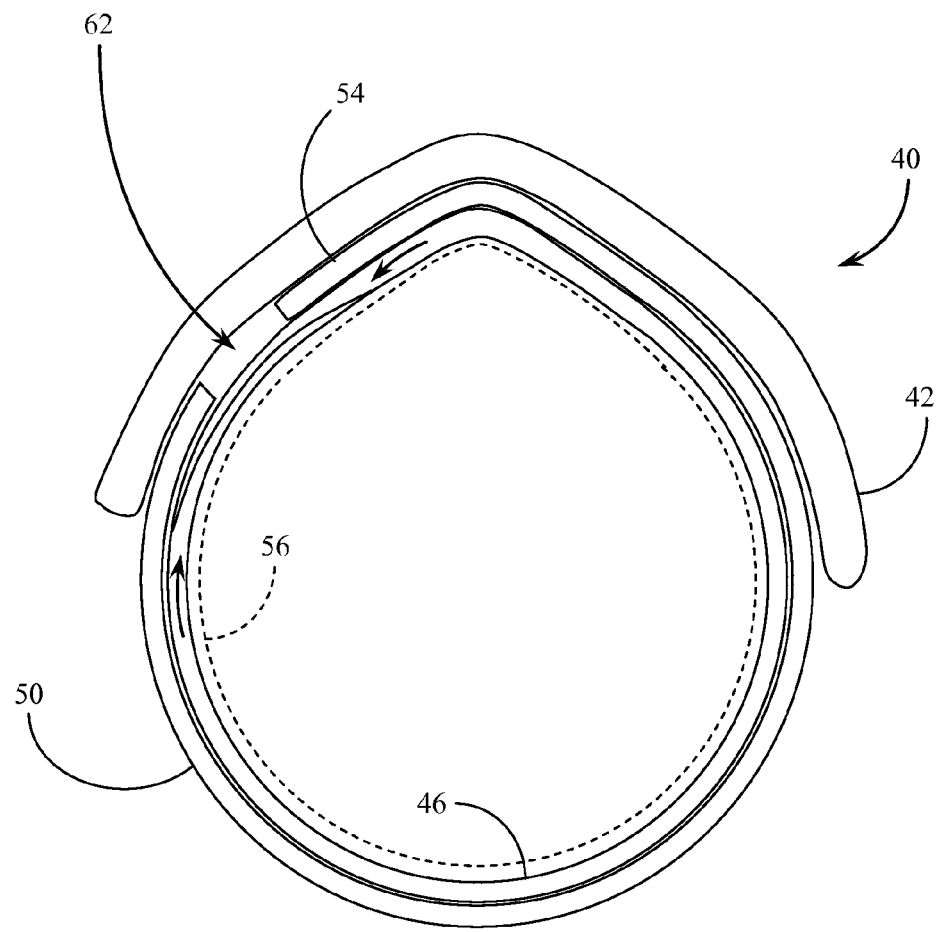
FIG. 2B is a diagram of the top view of the complete calf shell of the ankle/foot orthotic system of the present invention.

FIG. 2B is a diagram of the top view of the complete calf shell of the ankle/foot orthotic system 40 of the present invention. A point of entry must exist either anteriorly, posteriorly, medially, or laterally depending on the diagnosis being treated. For simplicity, only an ankle-foot shell with an anteriolateral point of entry will be described and other variations may be derived from that description. FIG. 2B shows the leg 56 and the point of entry on the ankle foot shell 62. The ankle foot shell compression liner 46 is fitted to the posterior portion of the ankle foot shell 50. The compression liner 46 overlaps anteriorly beneath the anterior portion of the ankle foot shell 54. FIG. 5C is a diagram of the ankle foot shell compression liner 46 of the ankle/foot orthotic system including the interior ends 46a and exterior ends 46b.

The compression liner is ideally fabricated from a 35 durometer Ethylene-Vinyl Acetate for flexibility, comfort, and ease of fabrication, but may also be fabricated from other foam, plastic, or similar materials. The compression liner should be fastened to the ankle-foot shell by means of rivets or similar fasteners. The compression liner 46 should extend slightly beyond the proximal edges of the ankle-foot shell, down beyond the distal border of the gastrocnemius, and circumferentially should overlap anteriolaterally at the point of entry 62 as shown in FIG. 2B. When the compound closure system is tightened the compression liner overlap will increase, allowing for varying degrees of circumferential compression control. The compression liner should be made to a model of the patient's leg for optimal outcome, using industry standard fabricating procedures.

Figures 5A, 5B:
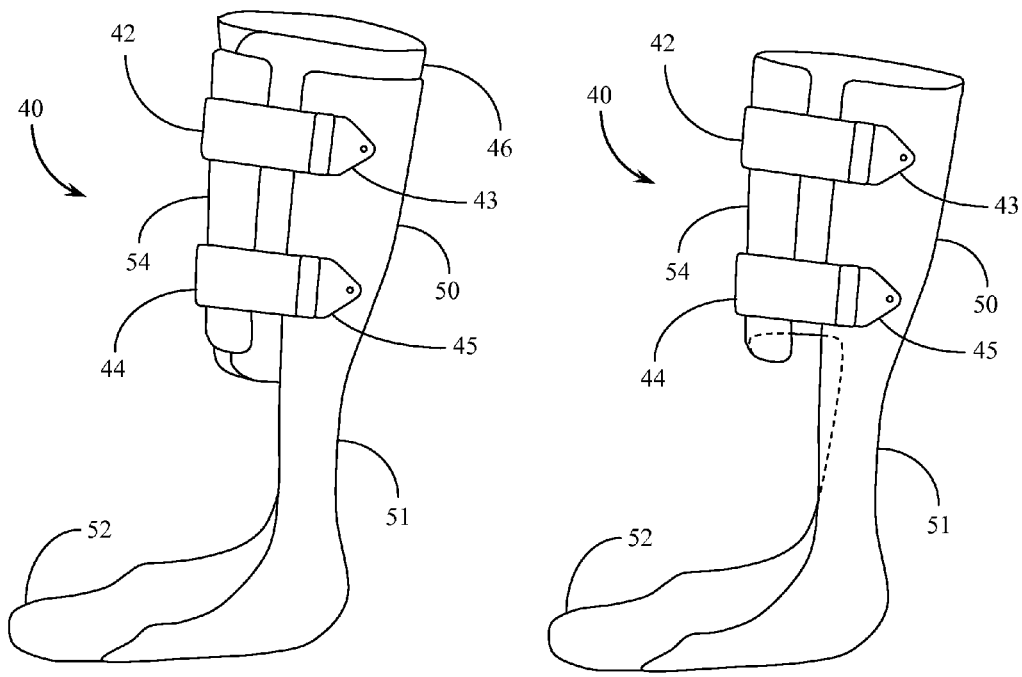
FIG. 5A is a lateral view of the ankle/foot orthotic system of the present invention.
FIG. 5B is a lateral view of the ankle/foot orthotic system of the present invention without the compression liner.
Figure 5C:
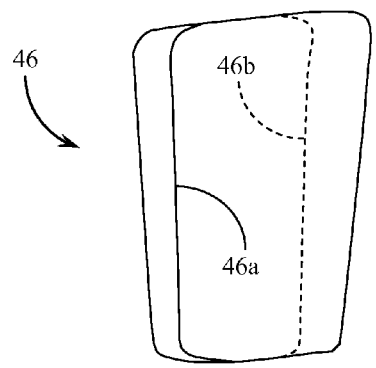
FIG. 5C is a diagram of the calf shell compression liner of the ankle/foot orthotic system of the present invention.

The entire configuration is secured by the proximal compound closure system 42 and 44 as shown in FIGS. 5A and 5B. The compound closure system consists ideally of two distal ratcheting ski-buckle type straps (also known as ladder straps) and two proximal hook and loop type straps which attach at both ends to the ankle-foot shell and span the point of entry. The distal straps are ideally of the ratcheting type since compression of the distal calf is more crucial to the efficacy of the design than compression of the proximal calf. The ratcheting straps take less effort to tighten and will maintain that tightened position better than hook and loop straps. However, the ratcheting straps may be difficult for the patient to align during donning and so simpler hook and loop straps are ideal proximally. However, any combination of ratcheting and/or hook and loop straps distally or proximally could conceivably be just as effective. The compound closure system, when tightened, will apply pressure through the flexible parts of the ankle-foot shell and onto the compression liner which will then compress the soft tissue of the calf. All elements are necessary for optimal function of the orthosis. Different materials may be used to accomplish the stated goal.

The design of the present invention can be used to unweight the ankle by capturing the conical shape of the distal end of the calf as shown in FIG. 3B. FIG. 3B is a diagram of the calf compression area of the ankle/foot orthotic system of the present invention. FIG. 3B shows the area of compression 66 on the distal end of the calf 74 below the knee 76. 100% unloading may be easily achieved in any situation using this design, but the amount of circumferential compression applied is fully adjustable which allows the amount of unloading to be fully adjustable, from 0% up to 100% and including any amount in between.

FIG. 5A is a lateral view of the ankle/foot orthotic system 40 of the present invention. FIG. 5B is a lateral view of the ankle/foot orthotic system 40 of the present invention without the compression liner. The ankle-foot shell is ideally fabricated from carbon fiber to achieve high strength with minimal weight, but may also be fabricated from plastic or other similar materials. The majority of the ankle-foot shell should ideally be rigid, with the material of the shell near the point of entry ideally being flexible. This can be done with widely available materials using industry standard laminating procedures. The standard design is one solid shell encompassing the plantar surface of the foot, the posterior of the ankle/foot complex, and at the height of the calf medially, laterally, anteriorly, and posteriorly encompassing the lower limb. The ankle-foot shell must effectively contain the lower limb and transfer weight from the compression liner to the ground.

The ankle foot shell should be made to a model of the patient's leg for optimal outcome, using standard industry laminating/fabricating procedures. The rigid posterior portion 50 of the ankle foot shell and the flexible anterior portion 54 of the ankle foot shell are connected by the proximal 42 and distal 44 compound closure systems. Both the proximal 42 and distal 44 closures are attached to the posterior portion 50 of the ankle foot shell (see points of attachment 43 and 45). The ankle portion 51 of the ankle foot shell extends from the calf portion to the foot platform 52. FIG. 5A shows the compression liner 46 which wraps around the calf.

Method of Using the KAFO and AFO Orthotic Systems of the Present Invention

When the patient applies the orthotic system of the present invention, he/she does so with the heel raised approximately ½ inch or more. The compound closure system and thereby the compression liner are tightened until the desired compression is achieved. Since the thigh and calf get larger distally to proximally, once the patient's weight is applied, the tissue eventually cannot drop down any further once it is choked off by the distal closure system. The key to achieving the desired reduction in weight-bearing is to elevate the heel consistently so as to be off the footplate of the ankle-foot shell once the thigh or calf stops its distal migration. If the heel 80 does not touch the footplate 32 of the ankle-foot shell (see FIG. 3C) then the leg is effectively 100% unloaded at all points distal to the distal border of the compression liner. If the heel does touch the footplate of the ankle-foot shell, then partial unloading has been achieved at all points distal to the distal border of the compression liner.

The orthotic system of the present invention is ideally made to a model of the patient's lower extremity. It is made from existing materials and is made in a similar fashion to previous KAFO/AFO designs. It is typically made by an orthotist or orthotic technician. This system, when applied and fabricated correctly, is able to accomplish 100% removal of loading forces at the knee and tibia and/or ankle and heel.

The KAFO/AFO designs in the prior art do not provide 100% removal of the weight carried through the knee and/or ankle solely using soft tissue compression. The compressing components of the present invention differ from other available designs and are critical to the success of the system. As discussed above, current systems designed to remove loading forces at the knee are few and rely at least partly on the axial skeleton for unloading. These are primarily referred to as ischial containment or quadrilateral brim type systems. As discussed previously, these approaches can be effective, but have many drawbacks. They must be made to exacting specifications, are very difficult to fabricate, and often require modification for patient comfort and compliance.

The method of using the present invention works through manipulation of soft tissue and is adjustable for comfort, control and unloading force. The present invention allows modification for partial unloading or no unloading at all. For example, a patient with a fracture through the head of the tibia may also have vascular compromise of blood flow to part of the head of the tibia. The physician may surgically fixate the fracture, but unweighting may be necessary to allow for revascularization. Once blood flow returns, the physician may want weight to be carried through the bone for improved healing. The design of the present invention permits adjustment of the orthosis to allow partial to full weight bearing, while maintaining necessary protection in the sagittal and frontal planes because the fracture is still healing. As described above, the design of the present invention is much easier to fabricate and duplicate, can be easily adjusted for loading requirements, and is better tolerated due to adjustability of compression force.

Although the present invention has been described in terms of the foregoing preferred embodiments, this description has been provided by way of explanation only, and is not intended to be construed as a limitation of the invention. Those skilled in the art will recognize modifications in the present invention to accommodate specific patient requirements. Such modifications as to structure, materials, and method of use, and even the specific arrangement of components, where such modifications are coincidental to the specific patient requirements, do not necessarily depart from the spirit and scope of the invention.

We claim:

1. An orthotic system for bearing all or a portion of the weight of a leg of an individual, the system comprising:
   a two part thigh shell comprising:
      an anterior component extending down a major portion of the front of the thigh;
      and a posterior component separate from the anterior component, the posterior component extending down a major portion of the back and sides of the thigh;

wherein the two part thigh shell is configured to fully encompass the thigh of the individual;

a fully adjustable compound closure system attached to the two part thigh shell between the anterior and posterior components;

a calf shell comprising a calf portion extending down a major portion of the back and sides of the calf, an ankle portion, and foot platform;

metal uprights hingedly connecting the thigh shell to the calf shell; and a compression liner having a proximal border and a distal border positioned interior to the thigh shell and configured to encompass the thigh of the individual;

wherein the two part thigh shell and the compression liner circumferentially compress the soft tissue of the thigh so that when the compound closure system is tightened, loading forces on the leg at all points distal to the two part thigh shell and the distal border of the compression liner are lessened.

2. The orthotic system of claim 1 wherein the fully adjustable compound closure system is comprised of two parts: proximal for positioning and distal for tightening.

3. The orthotic system of claim 2 wherein the proximal part of the fully adjustable compound closure system comprises hook and loop material.

4. The orthotic system of claim 2 wherein the distal part of the fully adjustable compound closure system comprises ladder strap material.

5. A method for reducing loading forces at the knee and tibia by variable circumferential compression of soft tissue of the thigh on the leg of an individual by a knee ankle foot orthotic system which utilizes a compression liner, thigh shell, metal uprights, calf shell, foot platform and compound closure system, the method comprising the steps of:

applying the orthotic system with the heel of the individual raised at least ½ inch above the foot platform of the calf shell;

tightening the compound closure system around the compression liner and thigh shell around the thigh of the individual;

applying the weight of the individual to the leg;

allowing the tissue of the thigh to drop down within the compression liner until further movement is halted by the compound closure system;

assessing the position of the heel of the individual above the foot platform of the calf shell; and adjusting the compound closure system to maintain the desired degree of elevation of the heel above the foot platform.

6. The method of claim 5, wherein the heel does not touch the foot platform and the desired degree of elevation of the heel above the foot platform results in reducing loading forces at the knee and tibia by 100 percent.

7. The method of claim 5, wherein the heel touches the foot platform and the desired degree of elevation of the heel above the foot platform results in reducing loading forces at the knee and tibia by less than 100 percent.

8. A method for reducing loading forces at the ankle and heel by variable circumferential compression of soft tissue of the calf on the leg of an individual by an ankle foot orthotic system which utilizes a compression liner, ankle foot shell, foot platform and compound closure system, the method comprising the steps of:

applying the orthotic system with the heel of the individual raised at least ½ inch above the foot platform of the ankle foot shell;

tightening the compound closure system around the compression liner and ankle foot shell around the calf of the individual;

applying the weight of the individual to the leg;

allowing the tissue of the calf to drop down within the compression liner until further movement is halted by the compound closure system;

assessing the position of the heel of the individual above the foot platform of the ankle foot shell; and adjusting the compound closure system to maintain the desired degree of elevation of the heel above the foot platform.

9. The method of claim 8, wherein the heel does not touch the foot platform and the desired degree of elevation of the heel above the foot platform results in reducing loading forces at the ankle and heel by 100 percent.

10. The method of claim 8, wherein the heel touches the foot platform and the desired degree of elevation of the heel above the foot platform results in reducing loading forces at the ankle and heel by less than 100 percent.

* * * * *